US011253719B2

(12) United States Patent
Strahan et al.

(10) Patent No.: US 11,253,719 B2
(45) Date of Patent: Feb. 22, 2022

(54) PHOTOBIOMODULATION THERAPY SYSTEMS AND METHODS

(71) Applicant: Joovv, Inc., San Clemente, CA (US)

(72) Inventors: Justin Strahan, San Clemente, CA (US); Scott Nelson, San Clemente, CA (US)

(73) Assignee: JOOVV, INC., San Clemente, CA (US)

( * ) Notice: Subject to any disclaimer, the term of this patent is extended or adjusted under 35 U.S.C. 154(b) by 193 days.

(21) Appl. No.: 16/598,033

(22) Filed: Oct. 10, 2019

(65) Prior Publication Data

US 2020/0197718 A1   Jun. 25, 2020

Related U.S. Application Data

(63) Continuation of application No. 16/584,784, filed on Sep. 26, 2019, now Pat. No. 10,639,495, and a
(Continued)

(51) Int. Cl.
*A61N 5/06* (2006.01)

(52) U.S. Cl.
CPC .......... *A61N 5/06* (2013.01); *A61N 2005/064* (2013.01); *A61N 2005/0629* (2013.01);
(Continued)

(58) Field of Classification Search
CPC .................... A61N 5/06; A61N 5/0616; A61N 2005/0636; A61N 2005/064;
(Continued)

(56) References Cited

U.S. PATENT DOCUMENTS

| 1,660,794 A | 2/1928 | Hudson |
| 2,327,346 A | 8/1943 | Furedy |

(Continued)

FOREIGN PATENT DOCUMENTS

| KR | 101244434 B1 | 3/2013 |
| WO | 2018152278 | 8/2018 |

(Continued)

OTHER PUBLICATIONS

PCT International Search Report and Written Opinion in International Application No. PCT/US2019/059845, dated Dec. 11, 2019, 7 pages.
(Continued)

*Primary Examiner* — Tammie K Marlen
(74) *Attorney, Agent, or Firm* — Wesley E. Schwie, Esq.; Gallium Law

(57) ABSTRACT

Photobiomodulation therapy systems provide a highly effective way to treat many common ailments to the human body. Many embodiments described herein enable two or more light therapy devices to be communicatively coupled together in various ways. In some embodiments, the light therapy system includes a first light device and a second light device arranged and configured to be communicatively coupled to the first light device. Each of the light devices may include a housing, a communication module, and a plurality of lights arranged and configured to emit at least one of red light and near infrared light.

20 Claims, 10 Drawing Sheets

Related U.S. Application Data continuation of application No. 16/227,289, filed on Dec. 20, 2018, now Pat. No. 10,478,635.

(52) U.S. Cl.
CPC ............... *A61N 2005/0659* (2013.01); *A61N 2005/0663* (2013.01)

(58) Field of Classification Search
CPC .... A61N 2005/0663; A61N 2005/0659; A61N 2005/6658; A61N 2005/0629
See application file for complete search history.

(56) References Cited

U.S. PATENT DOCUMENTS

| | | | |
|---|---|---|---|
| 3,416,852 A | 12/1968 | Goldbeck |
| 4,312,361 A | 1/1982 | Nicholson |
| 4,673,152 A | 6/1987 | Brown |
| 4,736,555 A | 4/1988 | Nagare |
| 4,740,707 A | 4/1988 | Thaw |
| 4,844,069 A | 7/1989 | Mori |
| 5,515,900 A | 5/1996 | West |
| 5,616,140 A | 4/1997 | Prescott |
| 5,645,578 A | 7/1997 | Daffer |
| 5,698,866 A | 12/1997 | Doiron |
| 5,733,032 A | 3/1998 | Bolta |
| 5,759,139 A | 6/1998 | Wright |
| 5,761,839 A | 6/1998 | Heikkila |
| 5,800,478 A | 9/1998 | Chen |
| 5,996,728 A | 12/1999 | Stark |
| 6,054,968 A | 4/2000 | De Matteo |
| 6,290,713 B1 | 9/2001 | Russell |
| 6,494,910 B1 | 12/2002 | Ganem |
| 6,508,262 B1 | 1/2003 | Takayama |
| 6,626,932 B2 | 9/2003 | Whitehurst |
| 6,645,230 B2 | 11/2003 | Whitehurst |
| 6,663,659 B2 | 12/2003 | McDaniel |
| 6,853,151 B2 | 2/2005 | Leong |
| 6,870,673 B2 | 3/2005 | Cromer |
| 6,896,693 B2 | 5/2005 | Sullivan |
| 6,955,684 B2 | 10/2005 | Savage |
| 7,033,381 B1 | 4/2006 | Larsen |
| 7,578,600 B2 | 8/2009 | Czajkowski |
| 7,863,641 B2 | 1/2011 | Dahm |
| 7,932,482 B2 | 4/2011 | Norwood |
| 8,043,349 B2 | 10/2011 | Springer |
| 8,066,403 B2 | 11/2011 | Sanfilippo |
| 8,337,538 B1 | 12/2012 | Ford |
| 8,376,602 B2 | 2/2013 | Klipstein |
| 8,425,577 B2 | 4/2013 | Vargas |
| 8,454,214 B2 | 6/2013 | Kazaoka |
| 8,481,982 B2 | 7/2013 | Johnson |
| 9,227,082 B2 | 1/2016 | McDaniel |
| 9,311,847 B2 | 4/2016 | Hall |
| 9,353,924 B2 | 5/2016 | Scarlata |
| 9,399,146 B2 | 7/2016 | Jones |
| 9,416,551 B2 | 8/2016 | Hall |
| 9,440,041 B1 | 9/2016 | Lacayo |
| 9,551,893 B2 | 1/2017 | An |
| 9,707,665 B1 | 7/2017 | Smith |
| 9,852,666 B2 | 12/2017 | Ward |
| 9,884,204 B1 | 2/2018 | Dolleris |
| 9,943,042 B2 | 4/2018 | Thosteson |
| 10,064,940 B2 | 9/2018 | Nager |
| 10,357,567 B1 | 7/2019 | Lundahl |
| 10,363,434 B2 | 7/2019 | Marchese |
| 10,440,794 B2 | 10/2019 | Alexander |
| D877,919 S | 3/2020 | Strahan |
| D877,920 S | 3/2020 | Nelson |
| D877,921 S | 3/2020 | Nelson |
| D877,922 S | 3/2020 | Strahan |
| D877,923 S | 3/2020 | Strahan |
| 10,632,325 B2 | 4/2020 | Lim |
| 10,672,306 B1 | 6/2020 | Whidden |
| 10,706,770 B2 | 7/2020 | Hall |
| D892,343 S | 8/2020 | Strahan |
| D892,344 S | 8/2020 | Nelson |
| D892,345 S | 8/2020 | Strahan |
| D893,737 S | 8/2020 | Nelson |
| D895,822 S | 9/2020 | Nelson |
| 10,828,505 B2 | 11/2020 | Nelson et al. |
| 10,881,550 B2 | 1/2021 | Tedford |
| 11,033,752 B2 | 6/2021 | Strahan |
| 2002/0198575 A1 | 12/2002 | Sullivan |
| 2003/0009205 A1 | 1/2003 | Biel |
| 2003/0188378 A1 | 10/2003 | Brunelle |
| 2003/0216795 A1 | 11/2003 | Harth |
| 2003/0233138 A1 | 12/2003 | Spooner |
| 2004/0008523 A1 | 1/2004 | Butler |
| 2004/0014199 A1 | 1/2004 | Streeter |
| 2004/0068305 A1 | 4/2004 | Bansal |
| 2004/0162596 A1 | 8/2004 | Altshuler |
| 2004/0188573 A1 | 9/2004 | Weatherly |
| 2004/0193234 A1 | 9/2004 | Butler |
| 2005/0075703 A1 | 4/2005 | Larsen |
| 2005/0085875 A1 | 4/2005 | Van Zuylen |
| 2005/0116667 A1 | 6/2005 | Mueller |
| 2005/0210722 A1 | 9/2005 | Graef |
| 2005/0230573 A1 | 10/2005 | Ligertwood |
| 2005/0237739 A1 | 10/2005 | Lee |
| 2006/0007059 A1 | 1/2006 | Bell |
| 2006/0020308 A1 | 1/2006 | Muldner |
| 2006/0030908 A1 | 2/2006 | Powell |
| 2006/0217787 A1 | 9/2006 | Olson |
| 2006/0217789 A1 | 9/2006 | Perez |
| 2006/0229689 A1 | 10/2006 | Ferguson |
| 2006/0241726 A1 | 10/2006 | Whitehurst |
| 2007/0038206 A1 | 2/2007 | Altshuler |
| 2007/0068055 A1 | 3/2007 | Segan |
| 2007/0084108 A1 | 4/2007 | Hertlein |
| 2007/0129776 A1 | 6/2007 | Robins |
| 2007/0129777 A1 | 6/2007 | Bolta |
| 2007/0217199 A1 | 9/2007 | Adam |
| 2007/0276455 A1 | 11/2007 | Fiset |
| 2008/0046044 A1 | 2/2008 | Jahnigen |
| 2008/0091250 A1 | 4/2008 | Powell |
| 2008/0114418 A1 | 5/2008 | Myeong |
| 2008/0119831 A1 | 5/2008 | Myeong |
| 2008/0141572 A1 | 6/2008 | Tomich |
| 2008/0210659 A1 | 9/2008 | McKinney |
| 2008/0269849 A1 | 10/2008 | Lewis |
| 2008/0306576 A1 | 12/2008 | Boyden |
| 2008/0312721 A1 | 12/2008 | Lemieux |
| 2009/0012588 A1 | 1/2009 | Springer |
| 2009/0058153 A1 | 3/2009 | Shafer |
| 2009/0262533 A1 | 10/2009 | Liu |
| 2009/0288340 A1 | 11/2009 | Hess |
| 2009/0318908 A1 | 12/2009 | Van Pieterson |
| 2010/0045175 A1 | 2/2010 | Mathai |
| 2010/0045189 A1 | 2/2010 | Storch |
| 2010/0076529 A1 | 3/2010 | Tucker |
| 2010/0265711 A1 | 10/2010 | Lee |
| 2010/0277105 A1 | 11/2010 | Oyama |
| 2010/0303603 A1 | 12/2010 | Galante |
| 2010/0309659 A1 | 12/2010 | Jenny |
| 2010/0324611 A1 | 12/2010 | Deming |
| 2011/0054573 A1 | 3/2011 | Mitchell |
| 2011/0176297 A1 | 7/2011 | Hsia |
| 2012/0019490 A1 | 1/2012 | Huang |
| 2012/0020109 A1 | 1/2012 | Kim |
| 2012/0030873 A1 | 2/2012 | Turtzo |
| 2012/0075871 A1 | 3/2012 | Chen |
| 2012/0104977 A1 | 5/2012 | McKenzie |
| 2012/0243227 A1 | 9/2012 | Shimizu |
| 2012/0283622 A1 | 11/2012 | Nath |
| 2012/0296260 A1 | 11/2012 | Vizethum |
| 2013/0101953 A1 | 4/2013 | Stone |
| 2013/0163235 A1 | 6/2013 | Chuang |
| 2013/0172963 A1 | 7/2013 | Moffat |
| 2013/0190842 A1 | 7/2013 | Hacco |
| 2013/0229802 A1 | 9/2013 | Fukushima |
| 2013/0279160 A1 | 10/2013 | Myers |
| 2013/0282082 A1 | 10/2013 | Daijo |
| 2013/0289673 A1 | 10/2013 | Matsubara |

(56) References Cited

U.S. PATENT DOCUMENTS

| | | |
|---|---|---|
| 2013/0301264 A1 | 11/2013 | Emericus |
| 2013/0304019 A1 | 11/2013 | Cooper |
| 2013/0304164 A1 | 11/2013 | Zanata |
| 2014/0031906 A1 | 1/2014 | Brezinski |
| 2014/0049942 A1 | 2/2014 | Chilton |
| 2014/0081357 A1 | 3/2014 | Legerton |
| 2014/0190537 A1 | 7/2014 | Benda |
| 2014/0197124 A1 | 7/2014 | McPhillips |
| 2014/0202493 A1 | 7/2014 | Zelickson |
| 2014/0226329 A1 | 8/2014 | Oraw |
| 2014/0241008 A1 | 8/2014 | Kim |
| 2014/0303547 A1 | 10/2014 | Loupis |
| 2015/0051671 A1 | 2/2015 | Browne |
| 2015/0062900 A1 | 3/2015 | Ferro |
| 2015/0112411 A1 | 4/2015 | Beckman |
| 2015/0198298 A1 | 7/2015 | Scarlata |
| 2015/0202455 A1 | 7/2015 | Williams |
| 2015/0265846 A1 | 9/2015 | Baird |
| 2015/0267907 A1 | 9/2015 | Thompson |
| 2015/0297914 A1 | 10/2015 | Hamid |
| 2015/0307332 A1 | 10/2015 | Huang |
| 2016/0015999 A1 | 1/2016 | Dabney |
| 2016/0016001 A1 | 1/2016 | Loupis |
| 2016/0076708 A1 | 3/2016 | Shirilla |
| 2016/0106950 A1 | 4/2016 | Vasapollo |
| 2016/0158574 A1 | 6/2016 | Eckhouse |
| 2016/0175610 A1 | 6/2016 | Livingston |
| 2016/0232822 A1 | 8/2016 | Ward |
| 2016/0286616 A1 | 9/2016 | Van De Ven |
| 2016/0367833 A1 | 12/2016 | Salinas |
| 2017/0007846 A1 | 1/2017 | Rabin |
| 2017/0028216 A1 | 2/2017 | Medendorp |
| 2017/0053570 A1 | 2/2017 | Cox |
| 2017/0074474 A1 | 3/2017 | Bailey |
| 2017/0080246 A1 | 3/2017 | Knight |
| 2017/0118838 A1 | 4/2017 | Williams |
| 2017/0131693 A1 | 5/2017 | Shurtleff |
| 2017/0274222 A1 | 9/2017 | Geyer |
| 2018/0008839 A1* | 1/2018 | Hamid ................ A61N 5/0617 |
| 2018/0036553 A1 | 2/2018 | Shiibashi |
| 2018/0043178 A1 | 2/2018 | Iguchi |
| 2018/0051862 A1 | 2/2018 | Meumann |
| 2018/0056087 A1 | 3/2018 | Ribeiro |
| 2018/0111001 A1 | 4/2018 | Segel |
| 2018/0141499 A1 | 5/2018 | Newman |
| 2018/0236259 A1 | 8/2018 | Nelson |
| 2018/0288840 A1 | 10/2018 | Kogure |
| 2018/0292055 A1 | 10/2018 | Moioli |
| 2018/0345034 A1 | 12/2018 | Butzloff |
| 2019/0030359 A1 | 1/2019 | Dijkstra |
| 2019/0167519 A1 | 6/2019 | Kaps |
| 2019/0388707 A1 | 12/2019 | Shenfarber |
| 2020/0060868 A1 | 2/2020 | Sivan |
| 2020/0086135 A1 | 3/2020 | Johnson |
| 2020/0121944 A1 | 4/2020 | Strahan |
| 2020/0269065 A1 | 8/2020 | Broeng |
| 2020/0324104 A1 | 10/2020 | Labuschagne |
| 2020/0353273 A1 | 11/2020 | Zucco |
| 2020/0360714 A1 | 11/2020 | Shterzer |

FOREIGN PATENT DOCUMENTS

| | | |
|---|---|---|
| WO | 2020086494 | 4/2020 |
| WO | 2020131235 | 6/2020 |

OTHER PUBLICATIONS

PCT International Search Report and Written Opinion in International Application No. PCT/US2019/057292, dated Jan. 7, 2020, 8 pages.

PCT International Search Report and Written Opinion in International Application No. PCT/US2020/038187, dated Aug. 19, 2020, 8 pages.

Kind Led Grow Lights, "Kind LED Grow Lights K5 Series Instructions"—Downloaded on Oct. 1, 2018 from https://www.kindledgrowlights.com/pages/k5-setup.

Mouser Electronics, "Enclosures and Racks"—Downloaded on Oct. 4, 2018 from http://www.mouser.com/catalog/catalogusd/648/dload/pdf/ENCLOSECTION.pdf; prior art publication at least as of 2015.

Kind LED Grow Lights, "Kind LED Grow Lights—Voted Best LED Grow Lights of 2014!"—Downloaded on Oct. 2, 2018 from https://www.youtube.com/watch?v=NQDWBXIMxrk; prior part publication at least as of May 26, 2017.

Wrethaoffgrid, "Ohuhu Pair of 1/8" Grow Light Rope Hanger Review—Downloaded on Oct. 5, 2018 from https://www.youtube.com/watch?v=gYCsNQ9LELM; prior art publication at least as of Sep. 29, 2016.

Oxo, "Oxo Over the Door Hooks & Racks"—Downloaded on Oct. 5, 2018 from https://www.youtube.com/watch?v=1WziS-a7LMI; prior part publication at least as of Feb. 11, 2014.

Woodworkers Store, "Swivel Mirror Screw"—Downloaded on Oct. 4, 2018 from http://go.rockler.com/tech/Swivel-Mirror-Screws-Instructions.pdf; prior art publication at least as of 1990.

Kind LED Grow Lights, "K5 Series XL1000 Indoor LED Grow Light"—Downloaded on Oct. 4, 2018 form https://www.kindledgrowlights.com/products/k5-xl1000.

Swedish Led Grow Lights, "300W Full Spectrum Led Grow Lights 85-265V 5730SMD USA/DE/AU/CA Stock Hanging Kit for Plants Veg Hydroponics Grow Led"—Downloaded on Jun. 5, 2017 from http://swedishledgrowlights.com/product/300w-full-spectrum-led-grow-lights-85-265v-5730smd-usa-de-au-ca-stock-hanging-kit-for-plants-veg-hydroponics-grow-led/.

Warp Light, "About the Quantum Light WARP 10®"—Downloaded on Sep. 19, 2019 from https://www.warp-light.com/Quantum_light_warp_10.html; prior art publication at least as of Nov. 30, 2012.

PCT International Search Report and Written Opinion in International Application No. PCT/US2018/018288, dated Oct. 29, 2018, 11 pages.

PCT International Preliminary Reporton Patentability in International Application No. PCT/US2018/018288, dated Aug. 20, 2019, 9 pages.

Green Envy Supply—How to Hang Light Reflector Using Rope Reel Ratchet Hangers—YouTube—video by user Green Envy Supply—First available Jan. 15, 2017—Available from Internet <URL: https://www.youtube.com/watch?v=W2z0m_7o-Y0>.

* cited by examiner

PHOTOBIOMODULATION THERAPY SYSTEMS AND METHODS

CROSS-REFERENCE TO RELATED APPLICATIONS

The entire contents of the following application are incorporated by reference herein: U.S. Pat. No. 10,828,505; filed Jun. 7, 2017; issued Nov. 10, 2020; and entitled THERAPEUTIC LIGHT SOURCE AND HANGING APPARATUS.

The entire contents of the following application are incorporated by reference herein: PCT Patent Application No. PCT/US18/18288; filed Mar. 1, 2018; and entitled THERAPEUTIC LIGHT SOURCE AND MOUNTING APPARATUS.

The entire contents of the following application are incorporated by reference herein: U.S. Pat. No. 11,033,752; filed Oct. 22, 2018; issued Jun. 15, 2021; and entitled PHOTOBIOMODULATION THERAPY SYSTEMS AND METHODS.

The entire contents of the following application are incorporated by reference herein: U.S. Pat. No. 10,478,635; filed Dec. 20, 2018; issued Nov. 19, 2019; and entitled PHOTOBIOMODULATION THERAPY SYSTEMS AND METHODS.

The entire contents of the following application are incorporated by reference herein: U.S. Pat. No. 10,639,495; filed Sep. 26, 2019; issued May 5, 2020; and entitled PHOTOBIOMODULATION THERAPY SYSTEMS AND METHODS.

BACKGROUND

Field

Various embodiments disclosed herein relate to photobiomodulation therapy systems and methods.

Description of Related Art

Photobiomodulation therapy (or light therapy) is a therapeutic technique that uses low-level wavelengths of light to improve health and treat a variety of health conditions, including skin issues, such as wrinkles, scars, and persistent wounds, among many other conditions. Similar to how plants use sunlight to heal and grow, humans and animals are able to harness these wavelengths of light and turn them into cellular energy. This treatment stimulates the body's natural healing processes.

Currently, there are a number of photobiomodulation therapy devices available on the market. However, many of these devices are too small and require multiple sessions to treat large areas. As a result, there is a need for a photobiomodulation therapy system that can treat several areas in fewer treatments.

SUMMARY

This disclosure includes a variety of communicatively coupled light therapy systems. In some embodiments, the light therapy system includes a first light therapy device comprising a first housing, a first plurality of lights arranged and configured to emit at least one of red light and near infrared light, and a first communication module communicatively coupled to the first plurality of lights. Some embodiments may also include a second light therapy device configured to be communicatively coupled to the first light therapy device. The second light therapy device may have a second housing, a second plurality of light arranged and configured to emit at least one of red light and near infrared light, and a second communication module communicatively coupled to the second plurality of lights.

The first communication module and the second communication module may be communicatively coupled via a wireless connection such as a Bluetooth connection. Alternatively, some embodiments may be communicatively coupled via a wired connection. In some embodiments, the first light therapy device further comprises a first plurality of communication ports coupled to the first housing and communicatively coupled to the first communication module. Similarly, the second light therapy device may also further comprise a second plurality of communication ports coupled to the second housing and communicatively coupled to the second communication module. The first light therapy device and the second light therapy device may me communicatively coupled via a wired connection from the first plurality of communication ports to the second plurality of communication ports.

The first light therapy device and the second light therapy device may each be configured to operate in one of a lead mode and a follow mode. When the first light therapy device operates in the lead mode and the second light therapy device operates in the follow mode, the second light device may perform operations as instructed by the first light therapy device.

In some embodiments, the first light therapy device and the second light therapy device may each be configured to operate in a neutral mode. For example, when the second light therapy device operates in the neutral mode the second light therapy device may operate independently of the first light therapy device.

To control the light therapy device, some embodiments may further comprise a first plurality of input buttons coupled to the first housing and communicatively coupled to the first communication module. Accordingly, the system may further include a second plurality of input buttons coupled to the second housing and communicatively coupled to the second communication module. The first plurality of input buttons may be arranged and configured to control a treatment time of the first light therapy device, cause light to be emitted from at least a portion of the first plurality of lights, and cause light not to be emitted from at least a portion of the first plurality of lights. Likewise, the second plurality of input buttons may be arranged and configured to control a treatment time of the second light therapy device, cause light to be emitted from at least a portion of the second plurality of lights, and cause light not to be emitted from at least a portion of the second plurality of lights.

In some embodiments, the first plurality of input buttons may comprise a first time button, a first play/pause button, and a first mode button. Similarly, the second plurality of input buttons may comprise a second time button, a second play/pause button, and a second mode button.

In some embodiments, a first press of the first time button may increase the treatment time of the first light therapy device by a predetermined amount of time. Similarly, a first press of the second time button may increase the treatment time of the second light therapy device by the predetermined amount of time. A first press of the first play/pause button may cause at least a portion of the first plurality of lights to emit light and a second press of the first play/pause button may cause at least a portion of the first plurality of lights to not emit light. Likewise, a first press of the second play/pause button may cause at least a portion of the second plurality of lights to emit light and a second press of the second play/pause button may cause at least a portion of the second plurality of lights to not emit light.

Even still, in some embodiments, a first press of the first mode button may cause at least a portion of red lights of the first plurality of lights to emit red light and at least a portion of near infrared lights of the first plurality of lights to not emit near infrared light. Furthermore, a second press of the first mode button may cause at least a portion of red lights of the first plurality of lights to not emit red light and at least a portion of near infrared lights of the first plurality of lights to emit near infrared light. Similarly, a first press of the second mode button may cause at least a portion of red lights of the second plurality of lights to emit red light and at least a portion of near infrared lights of the second plurality of lights to not emit near infrared light. Furthermore, a second press of the second mode button may cause at least a portion of red lights of the second plurality of lights to not emit red light and at least a portion of near infrared lights of the second plurality of lights to emit near infrared light.

To indicate which lights will be used during treatment, some embodiments of the system may further comprise a first pair of indication lights that may be coupled to the first housing and communicatively coupled to the first plurality of input buttons. In some embodiments, the first pair of indication lights may be arranged and configured to indicate whether a portion of red lights of the first plurality of lights is emitting red light and whether a portion of near infrared lights of the first plurality of lights is emitting near infrared light. Similarly, in some embodiments, the system further includes a second pair of indication lights coupled to the second housing and communicatively coupled to the second plurality of input buttons. The second pair of indication lights may be arranged and configured to indicate whether a portion of red lights of the second plurality of lights is emitting red light and whether a portion of near infrared lights of the second plurality of lights is emitting near infrared light.

BRIEF DESCRIPTION OF THE DRAWINGS

These and other features, aspects, and advantages are described below with reference to the drawings, which are intended to illustrate, but not to limit, the invention. In the drawings, like reference characters denote corresponding features consistently throughout similar embodiments.

DETAILED DESCRIPTION

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any system or device disclosed herein, the acts or operations of the system or device may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, methods, and/or procedures described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

INDEX OF COMPONENTS

10—Light therapy system
12—Light therapy device
14—Housing
16—Plurality of lights
24—Communication module
26—Plurality of communication ports
28—Communication Cable
70—Lead mode
80—Follow mode
90—Neutral mode
92—Power switch
100—Control panel
110—Plurality of buttons
112—Time button
114—Play/pause button
116—Mode button
120—Pair of indication lights

INTRODUCTION

Light therapy provides an alternative option for treating many common ailments and diseases. For example, when the human body is exposed to red light, blue light, green light, and/or near infrared light, subjects can expect to see improvement in multiple skin conditions, weight loss, muscle recovery, sexual performance, joint pain, and thyroid function. Instead of using prescription medications to solve these many problems, light therapy can be used in place of these traditional remedies to achieve safe and effective results.

Many top professionals have adopted light therapy, but oftentimes the light therapy devices and systems used are not big enough to treat an entire body at once. Accordingly, many embodiments described herein enable two or more light therapy devices to be communicatively coupled together to form a light therapy system. In doing so, the area of treatment can be expanded to reduce the time and number of treatments to achieve the desired results.

System Embodiments

Figure 1:
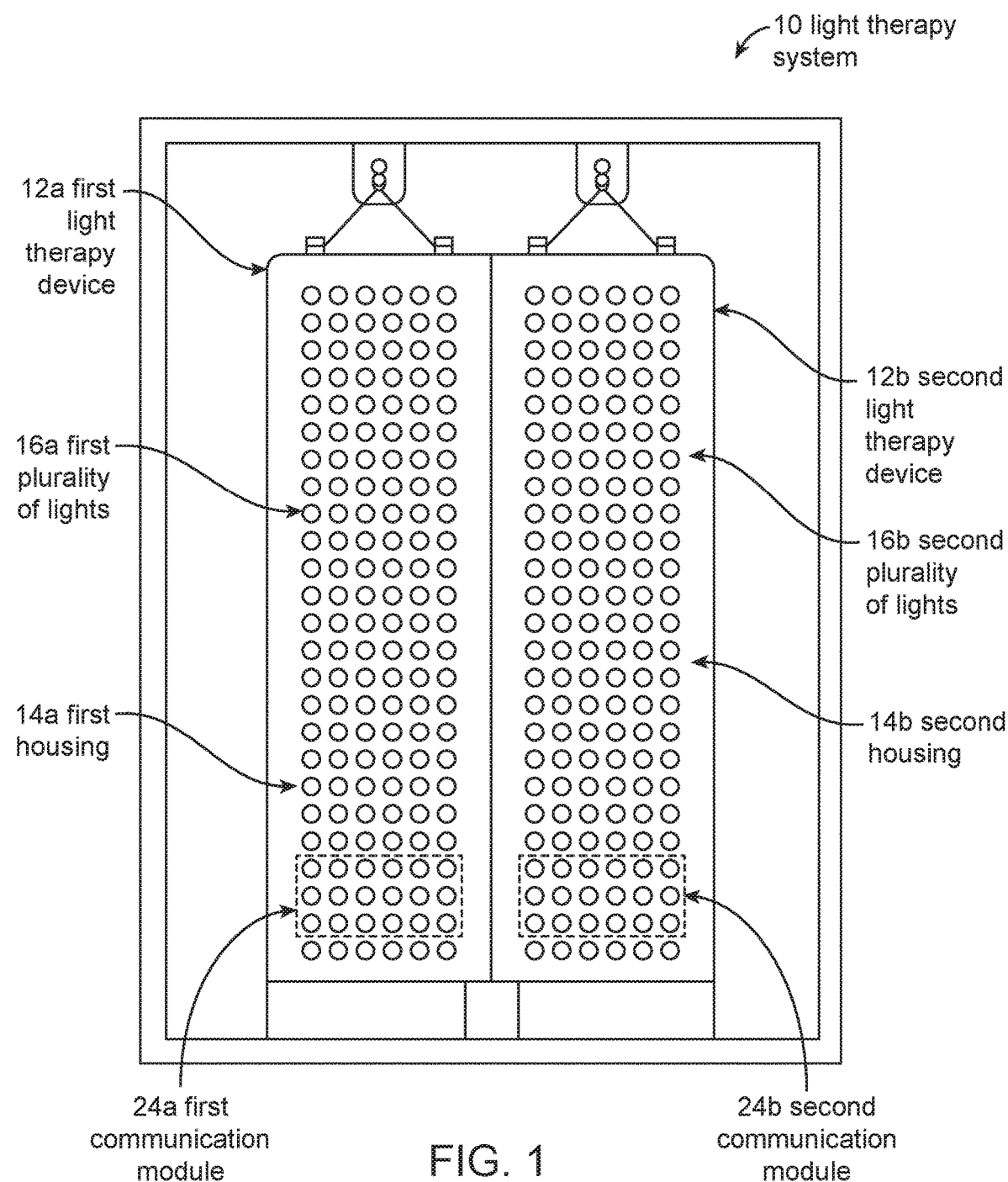
FIG. 1 illustrates a front view of a light therapy system, according to some embodiments.

FIG. 1 illustrates an embodiment of a light therapy system 10 having a first light therapy device 12a and a second light therapy device 12b. In some embodiments, the first light therapy device 12a may have a first housing 14a, a first plurality of lights 16a, and a first communication module 24a. The first plurality of lights 16a may be mechanically coupled to the first housing 14a. In some embodiments, the first plurality of lights 16a may be red lights, near infrared lights, or some combination of red lights and near infrared lights. The first communication module 24a may be communicatively coupled to the first plurality of lights 16a such that the first plurality of lights 16a may receive instructions and thereby operate in a specific manner.

Furthermore, FIG. 1 also shows the light therapy system 10 having a second light therapy device 12b, which is communicatively coupled to the first light therapy device 12a. Similar to the first light therapy device 12a, the second light therapy device 12b may include a second housing 14b, a second plurality of lights 16b, and a second communication module 24b. The second plurality of lights 16b may be mechanically coupled to the second housing 14b. In some embodiments, the second plurality of lights 16b may be red lights, near infrared lights, or some combination of red lights and near infrared lights. The second communication module 24b may be communicatively coupled to the second plurality of lights 16b such that the second plurality of lights 16b may also receive instructions.

In many embodiments, the light therapy devices 12 are communicatively coupled to each other. In this regard, the first therapy device 12a may be communicatively coupled to the second light therapy device 12b whereby either of the devices 12 is able to control the other respective device 12. Such functionality may allow one or more light devices 12 to act as one cohesive system to more effectively provide treatment for a patient.

Because multiple light therapy devices 12 may be communicatively coupled together, this may allow for the light therapy system 10 to be located in one location or various remote locations. For example, in some embodiments, a light therapy system 10a may comprise two or more light therapy devices communicatively coupled together and physically located within close proximity of each other, such as in the same treatment room. However, in some embodiments, a light therapy system 10b may comprise two or more light therapy devices communicatively coupled together but the two or more light therapy devices are physically located remotely with respect to each other, such as in different cities. Communicatively coupling remotely located light therapy devices 12 may be effective for a variety of scenarios, such as a clinician who is remotely located with respect to a patient and thereby wants to render treatment for the patient. The clinician may communicatively couple a light therapy device 12, or a remote computing device (e.g. a smartphone), located in the clinician's office to one or more light therapy devices 12 located nearby the patient. The clinician may thereby treat the patient, even though the clinician and patient are physically located in remote locations with respect to the other.

Figure 2:
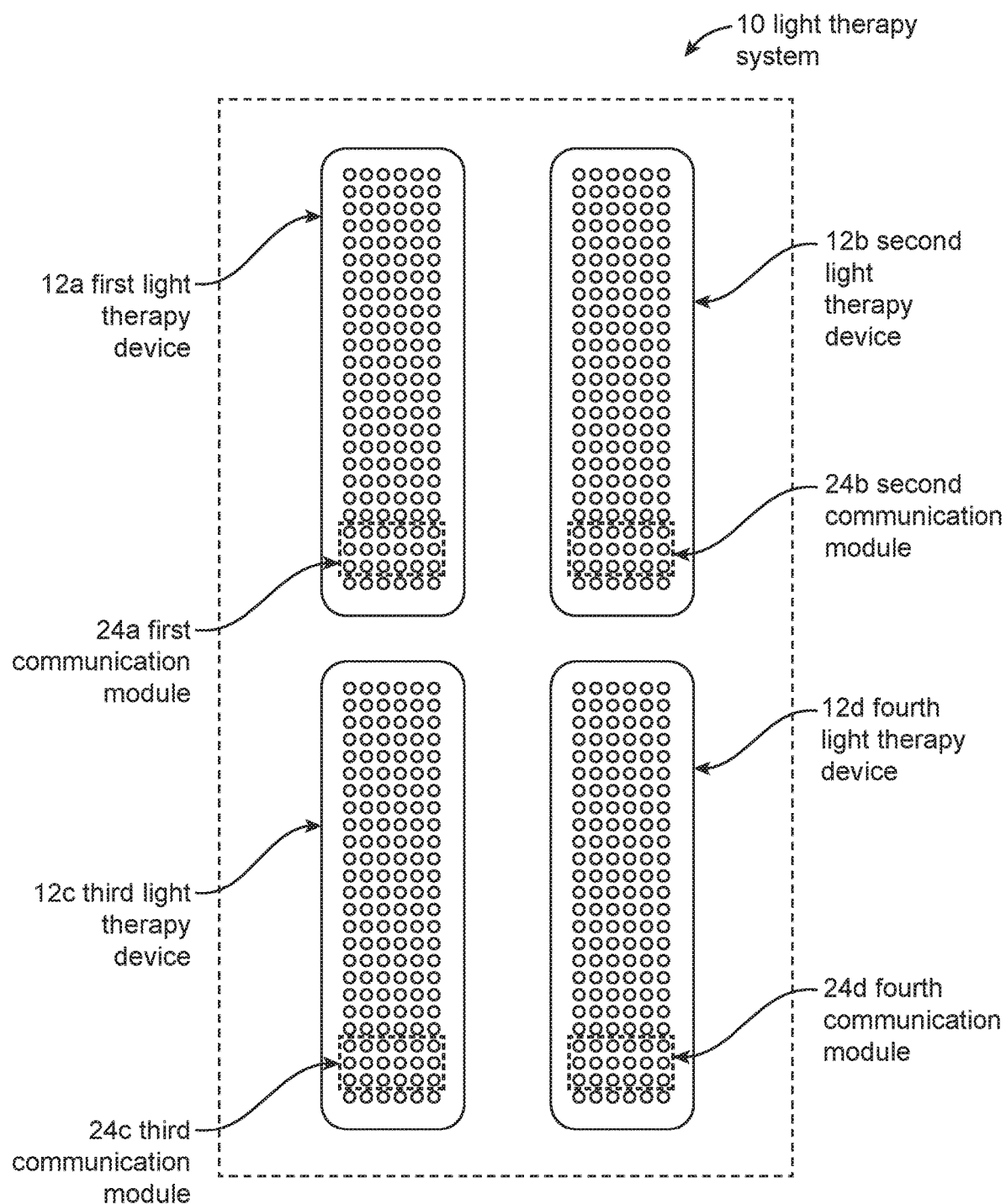
FIG. 2 illustrates a front view of a light therapy system communicatively coupled wirelessly, according to some embodiments.
Figure 3:
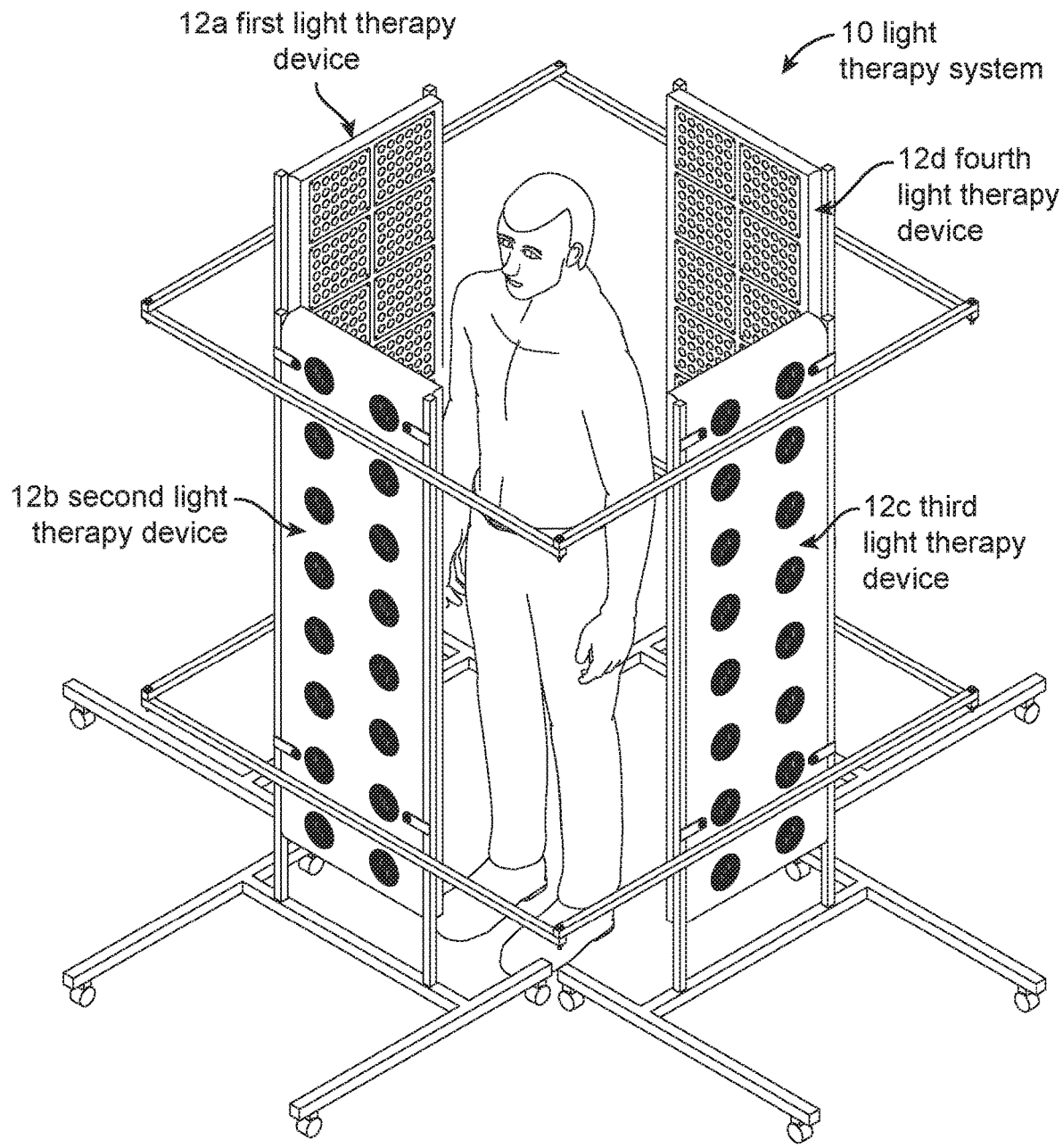
FIG. 3 illustrates a top perspective view of a light therapy system, according to some embodiments.

To achieve the communicative coupling, the devices 12 may be communicatively coupled via communication modules 24. For example, FIG. 2 depicts a light therapy system 10 including a first light therapy device 12a having a first communication module 24a, a second light therapy device 12b having a second communication module 24b, a third light therapy device 12c having a third communication module 24c, and a fourth light therapy device 12d having a fourth communication module 24d. FIG. 3 illustrates another embodiment of a light therapy system 10 in which there are multiple light therapy devices 12a, 12b, 12c, and 12d that are communicatively coupled wirelessly. In this embodiment, a user is standing in the middle of the light therapy system 10 to treat the entire body with light therapy simultaneously. The light therapy devices 12 may be communicatively coupled wirelessly by any suitable communication protocol, such as Zigbee, Bluetooth, BLE, Z-Wave, near-field communication (NFC), cellular network protocols (3G, 4G, 5G), Wi-Fi, and the like. The person of ordinary skill in the art may select a protocol that suits the needs and physical locations of the light therapy devices 12 being communicatively coupled together.

While FIGS. 1, 2, and 3 illustrate 2 or 4 light therapy devices in communication with each other; it should be appreciated that any number of light therapy devices may be communicatively coupled together. For example, in some embodiments, the light therapy system includes 3, 5, 6, 7, 8 or more devices communicatively coupled together. Generally, any number of devices may be communicatively coupled using any respective communication protocol.

Furthermore, the light therapy system 10 may also include other devices, such as remote computing devices (e.g. smartphone, tablet, computer, and the like), located remotely with respect to the light devices 12. In this regard, a plurality of light devices 12 may be communicatively coupled to one another, and the plurality of light devices 12 may further be communicatively coupled to a remote computing device operated by a third party. For example, a third party clinician or technician may communicatively couple their remote computing device to the light therapy system 10 to remotely communicate with the system 10. This may assist clinicians in providing treatment to patients, technicians in troubleshooting problems with the light therapy system, and the like.

Light therapy devices 12 may also be communicatively coupled via a wired connection. To communicatively couple light therapy devices 12 via a wired connection, some embodiments feature a plurality of communication ports 26 which may be located on the housing 14. In some embodiments, at least one port of the plurality of communication ports 26 may be configured to send signal from the first light therapy device 12a to the second light therapy device 12b. Similarly, at least one port of the plurality of communication ports 26 may be configured to receive signal from another light therapy device 12. In some embodiments, a communication cable 28 may be inserted into the pluralities of communication ports 26 to communicatively couple the light therapy devices 12.

Figure 4A:
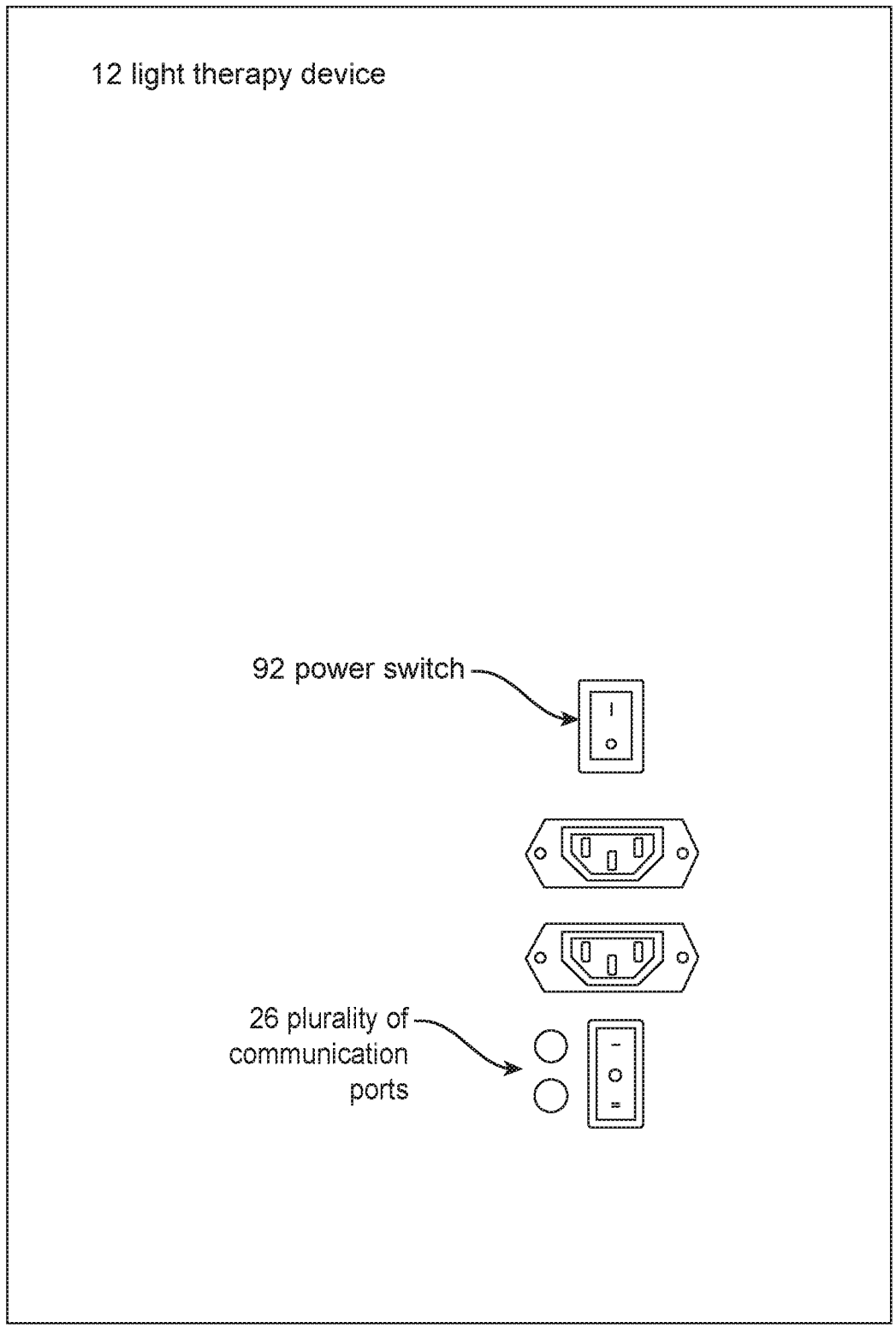
FIG. 4a illustrates a back view of a light therapy device, according to some embodiments.
Figure 4B:
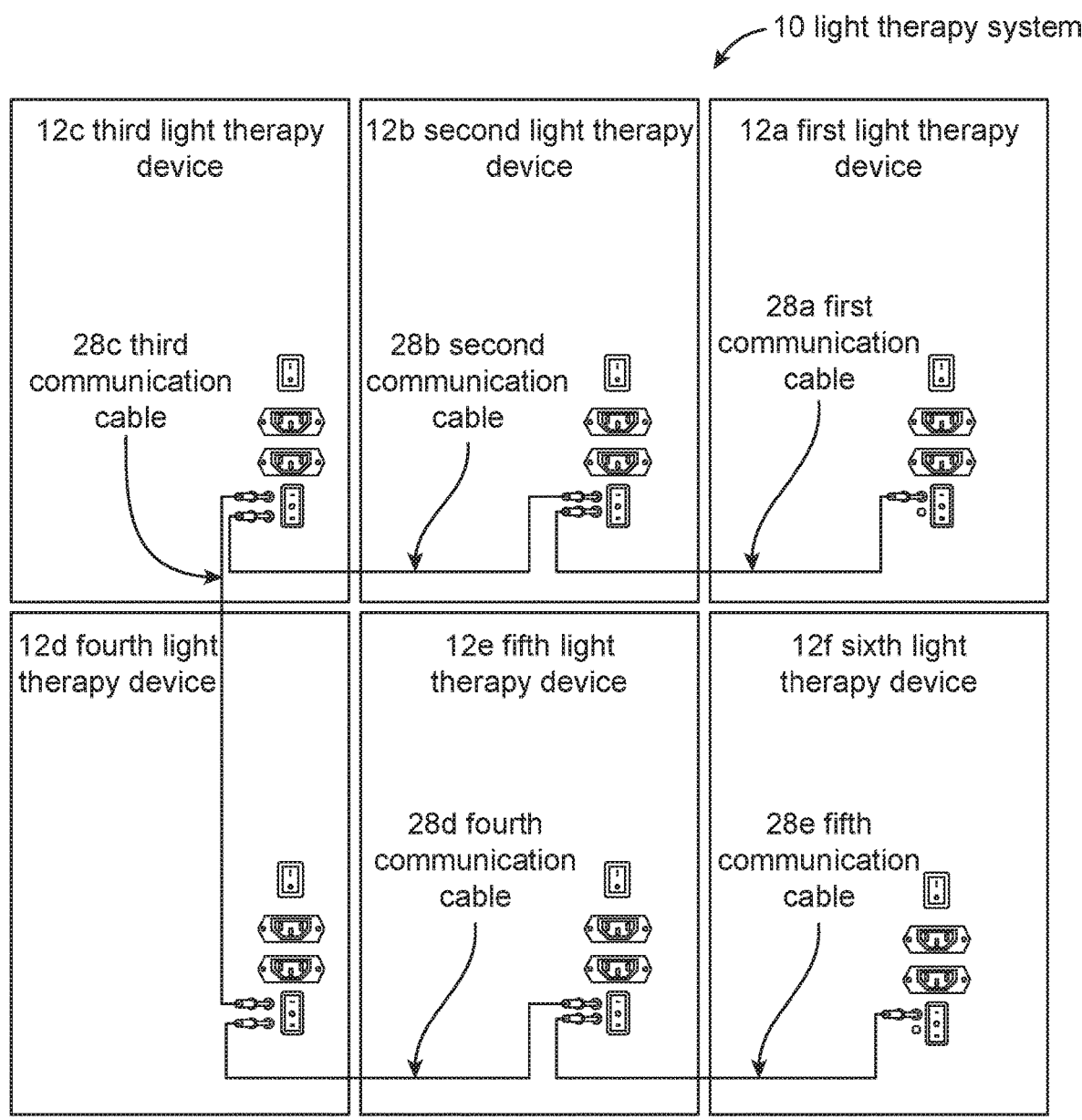
FIG. 4b illustrates a back view of a light therapy system communicatively coupled via a wired connection.

As shown in FIG. 4b, which illustrates the backside of a light therapy system 10, a plurality of light therapy devices 12 may be communicatively coupled together using communication cables 28 to thereby form the system 10. Communicatively coupling the light therapy devices 12 in this way allows the light therapy devices 12 to be controlled by one set of instructions. As shown in FIG. 4a, each light therapy device 12 may comprise a plurality of communication ports 26 used to communicatively couple more than one device 12 together via wires. As shown in FIG. 4b, a first light therapy device 12a is communicatively coupled to the second light therapy device 12b by a first communication cable 28a, which is inserted into the first plurality of communication ports 26a and the second plurality of communication ports 26b. In a similar fashion, the second light therapy device 12b may be communicatively coupled to a third light therapy device 12c by inserting a second communication cable 28b into the second plurality of communication ports 26b and the third plurality of communication ports 26c. A fourth light therapy device 12d may be communicatively coupled to the light therapy system 10 by inserting a third communication cable 28c into the third plurality of communication ports 26c and the fourth plurality of communication ports 26d. Similarly, a fifth light therapy device 12e may be communicatively coupled to the light therapy system 10 by inserting a fourth communication cable 28d into the fourth plurality of communication ports 26d and the fifth plurality of communication ports 26e. Finally, a sixth light therapy device 12f may be communicatively coupled to the light therapy system 10 by inserting a fifth communication cable 28e into the fifth plurality of communication ports 26e and a sixth plurality of communication ports 26f. Communicatively coupling the light therapy devices 12 in this way enables the entire light therapy system 10 to be controlled one set of input commands.

The embodiment depicted in FIG. 4b has six light therapy devices 12 communicatively coupled via communication cables 28. In some embodiments, there may only be two light therapy devices 12. In other embodiments, there may be more than six light therapy devices 12 communicatively coupled via a wired or a wireless connection. Additionally, the light therapy devices 12 may be communicatively coupled in series or in parallel. The light therapy system 10 of FIG. 4b is communicatively coupled in series. Alternatively, the first light therapy device 12a may communicatively couple to the second light therapy device 12b and the third light therapy device 12c directly. For example, the first communication cable 28a may be inserted into the first plurality of communication ports 26a and the second plurality of communications ports 26b. Similarly, the second communication cable 28b may also be inserted into the first plurality of communication ports 26a and the third plurality of communication ports 26c. This pattern may continue for as many light therapy devices 12 as necessary, or the light therapy devices 12 may be communicatively coupled in any combination of series and parallel wired connections.

To ensure that the light therapy devices 12 operate in the same way, some embodiments feature a lead mode 70 and a follow mode 80. A light therapy device 12 that is configured to be in the lead mode 70 may send operation instructions to all other light therapy devices 12 in the system 10. A light therapy device 12 that is configured to be in the follow mode 80 may receive operation instructions from a light therapy device 12 that is in the lead mode 70.

Figure 5:
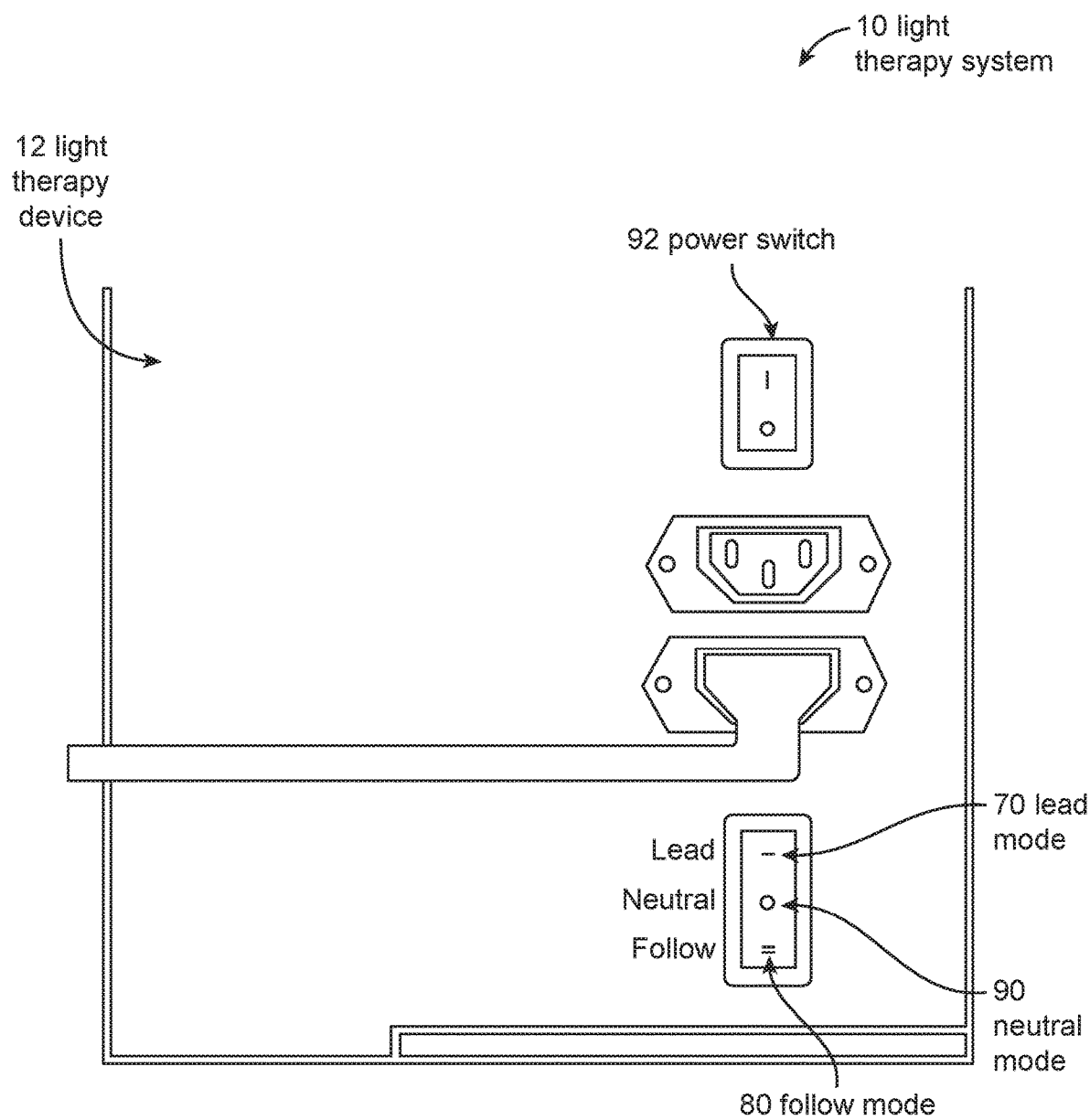
FIG. 5 illustrates a back view of a light therapy system, according to some embodiments.

FIG. 5 illustrates a light therapy system 10 with a first light therapy device 12a having a power switch 92, a lead mode 70, a follow mode 80, and a neutral mode 90. A user may thereby select the desired mode by switching a three-way toggle switch between lead mode 70, follow mode 80, and neutral mode 90. In some embodiments, a light therapy system 10 may comprise a first light therapy device 12a configured to be in the lead mode 70, while all other light therapy devices 12 are in the follow mode 80. Configuring the light therapy system 10 in this way may force the light therapy devices 12 to operate in the same way. In some embodiments, there may be more than one light therapy device 12 in the lead mode 70. For example, a light therapy system 10 may comprise six light therapy devices 12, whereby two light therapy devices 12 are in the lead mode and four light therapy devices 12 are in the follow mode. In such embodiments, either of the two light therapy devices 12 in the lead mode may control the other four light devices 12 in the follow mode. It should be appreciated that any number of light therapy devices may be in the follow mode 80.

A light therapy device 12 configured to be in neutral mode 90 may operate on its own and may ignore instructions sent from a light therapy device 12 in the lead mode 70. In this manner, the light therapy device(s) 12 in the neutral mode may ignore incoming signals. In some embodiments, there may be none, one, or more than one light therapy device 12 in the lead mode 70, none, one, or more than one light therapy device 12 in the follow mode 80, and none, one, or more than one light therapy device 12 in neutral mode 90. Any combination of light therapy devices 12 configured in the lead mode 70, the follow mode 80, and the neutral mode 90 may be used to achieve any combination of treatment types.

Figure 6A:
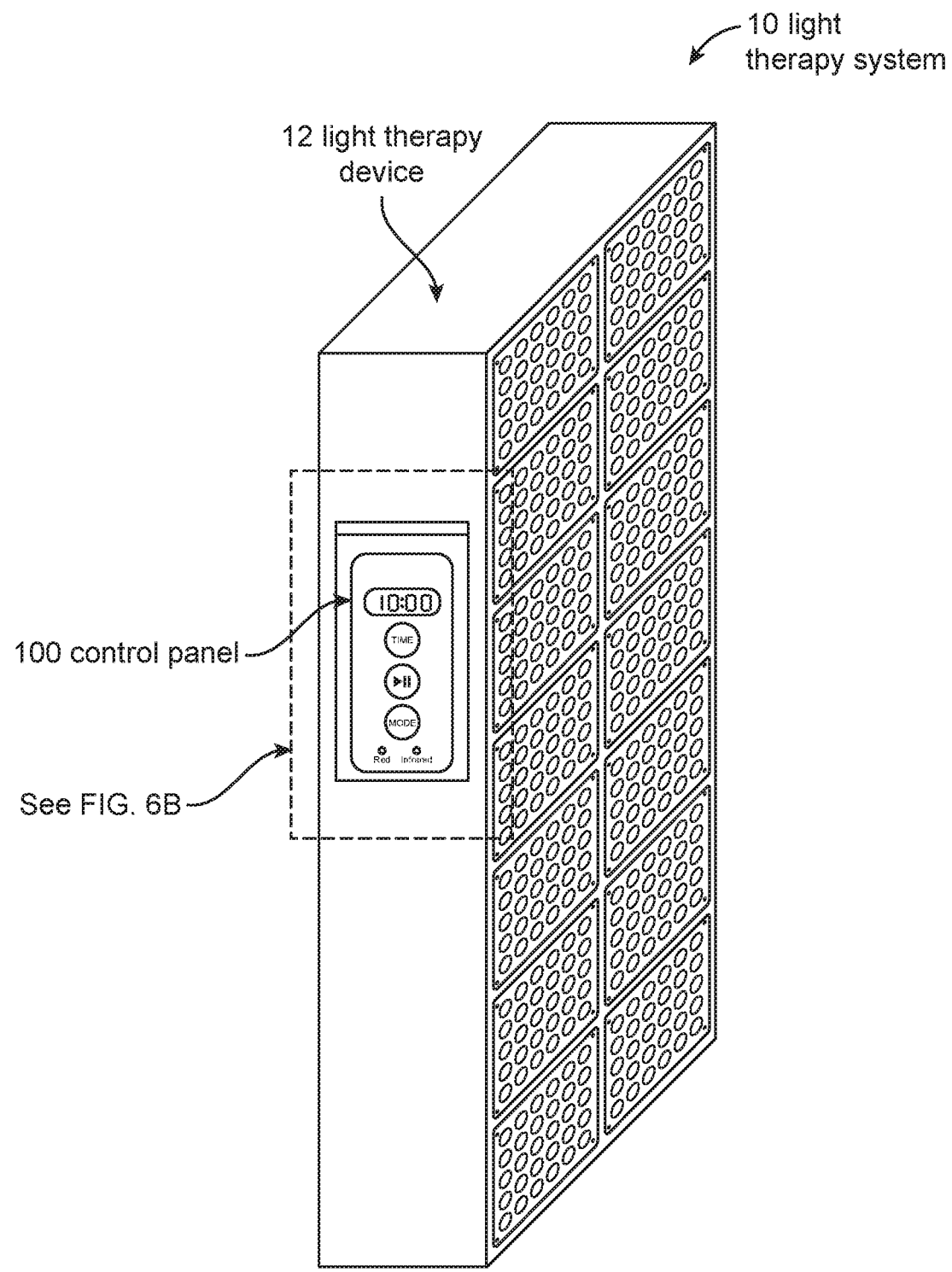
FIG. 6A illustrates a top left perspective view of a light therapy system, according to some embodiments.

As shown in FIG. 6a, in order to control the first light therapy device 12a, some embodiments feature a first control panel 100a located on the first housing 14a and communicatively coupled to the first communication module 24a. The first control panel 100a may allow a user to control a treatment time and cause at least a portion of the first plurality of lights 16a to either emit or not emit red light or near infrared light. Similarly, the second light therapy device 12b may have a second control panel 100b located on the second housing 14b and communicatively coupled to the second communication module 24b. The second control panel 100b may implement the same controls as the first control panel 100a.

Figure 6B:
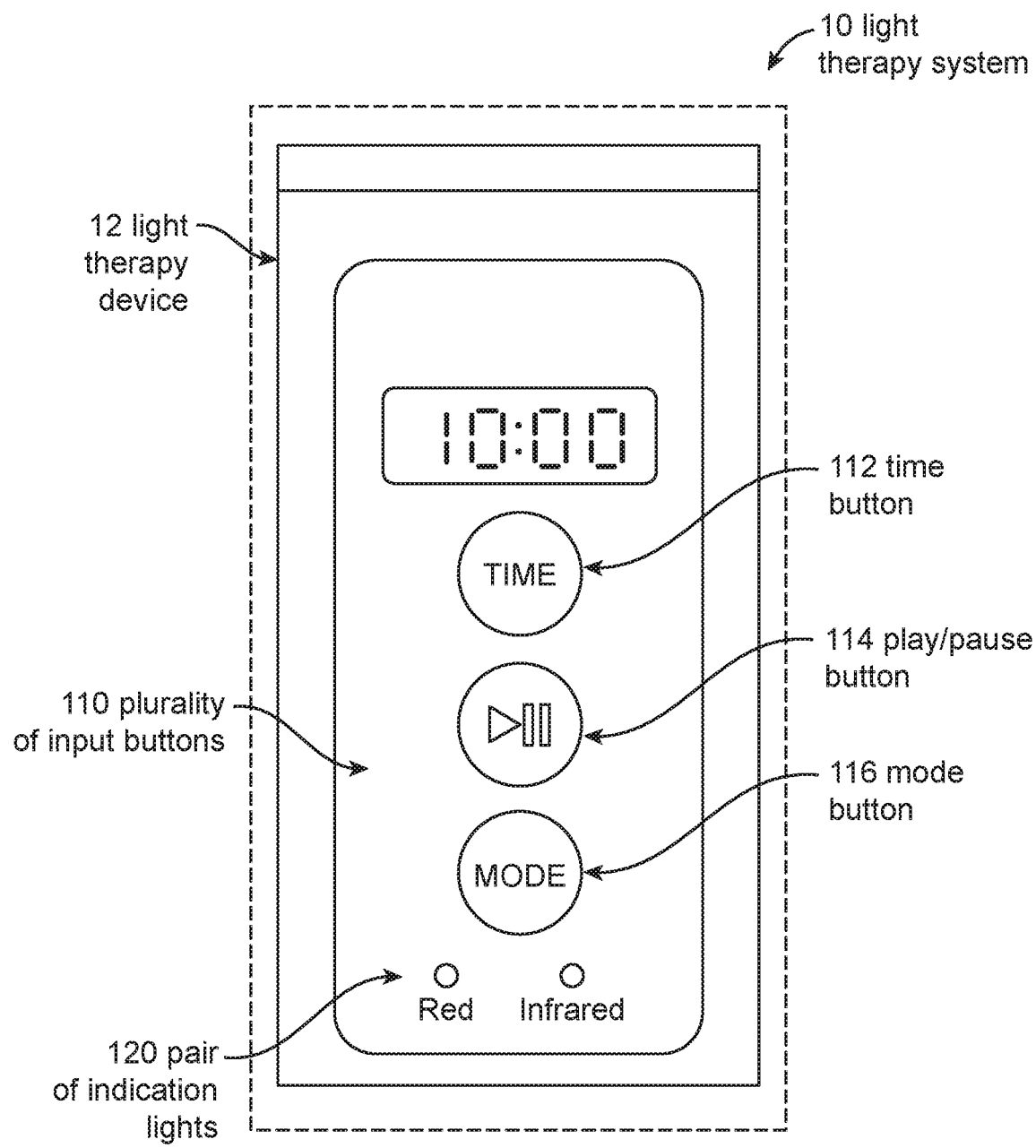
FIG. 6B illustrates a zoomed in view of a control panel, according to some embodiments.
Figure 7:
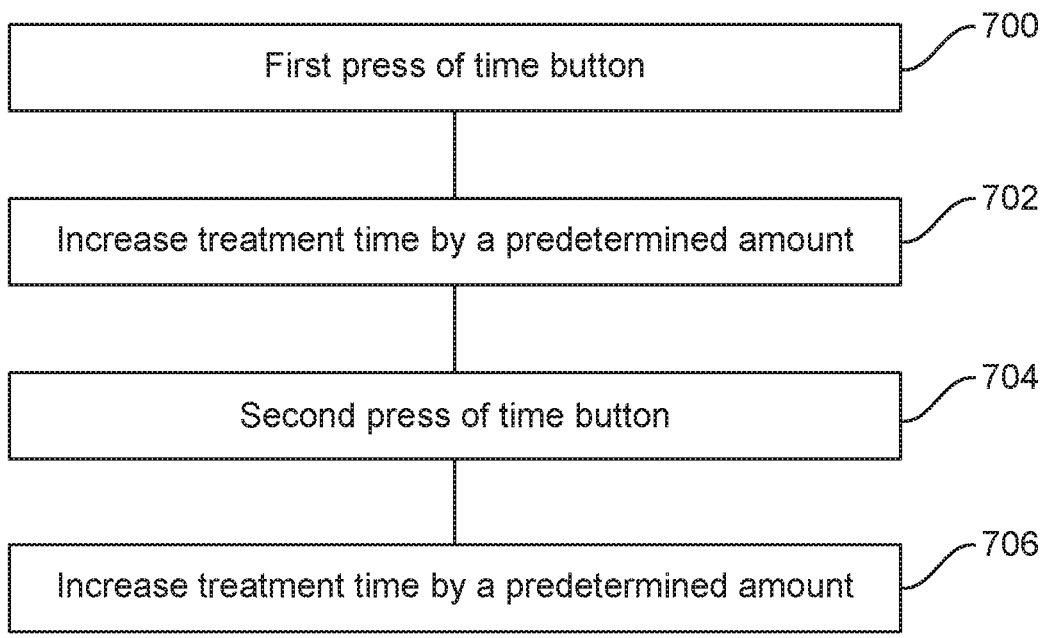
FIG. 7 illustrates a flow chart for operating the time button, according to some embodiments.
Figure 8:
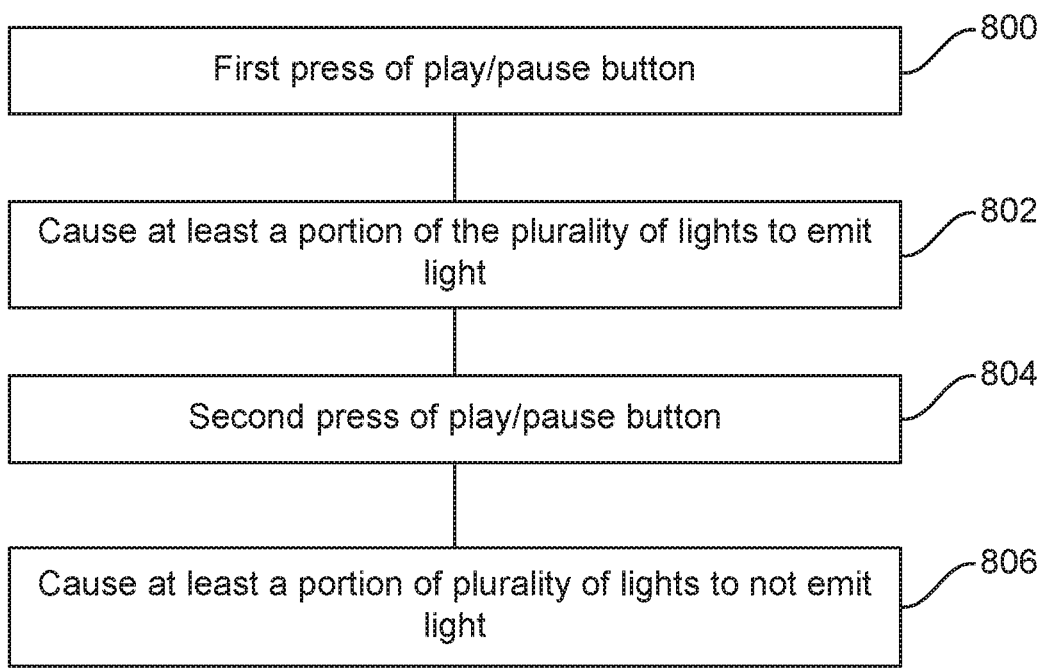
FIG. 8 illustrates a flow chart for operating the play/pause button, according to some embodiments.
Figure 9:
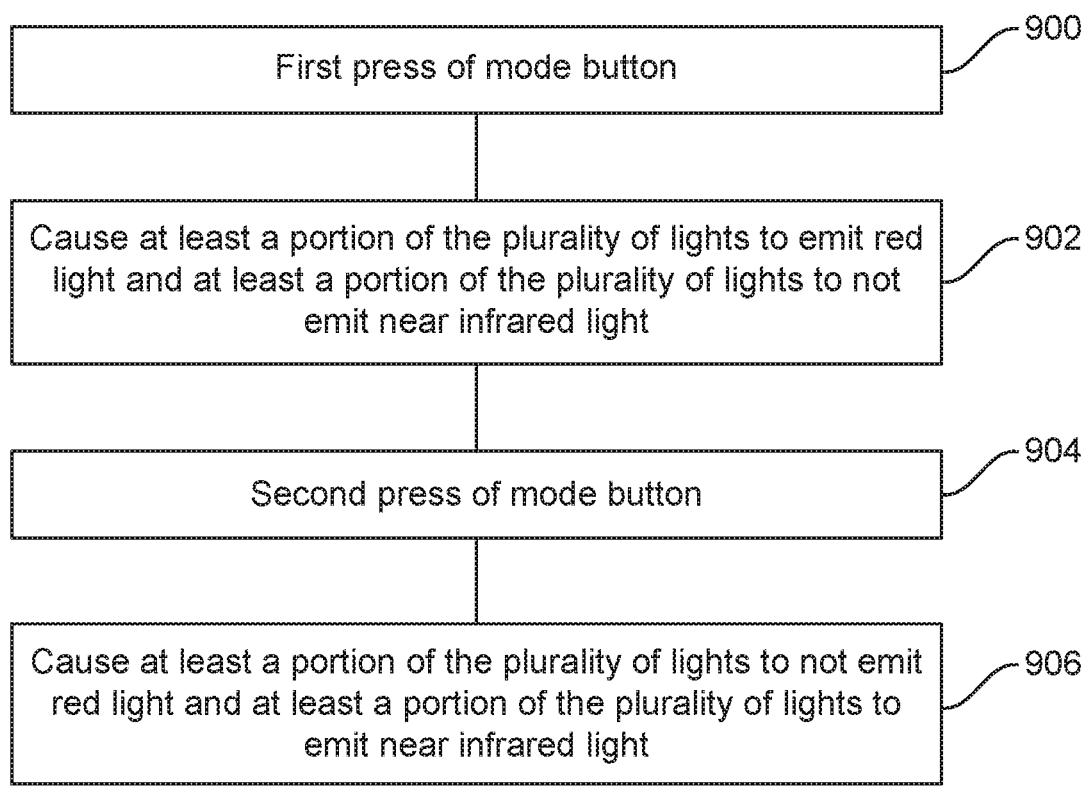
FIG. 9 illustrates a flow chart for operating the mode button, according to some embodiments.

FIG. 6a shows one embodiment of a light therapy system 10 with a first light therapy device 12a featuring a control panel 100. FIG. 6b shows a similar embodiment zoomed in to the control panel 100 having a plurality of input buttons 110, a time button 112, a play/pause button 114, a mode button 116, and a pair of indication lights 120. FIGS. 7, 8, and 9 show a flow chart of what each button may do when pressed.

In some embodiments, the plurality of input buttons 110 may have a time button 112 which, when pressed a first time 700, may be configured to increase the treatment time by a predetermined amount of time 702. In some embodiments, the predetermined amount of time may be one minute, five minutes, or any amount of time including negative amounts of time. Each additional press 704 of the time button 112 may increase the treatment time by the same predetermined amount of time 706. In some embodiments, the control panel 100 may be configured to have a predetermined maximum treatment time, for example twenty minutes. In embodiments such as these, if the treatment time is set to the predetermined maximum treatment time and the time button 112 is pressed once more the treatment time may change to a predetermined minimum treatment time instead of adding another predetermined amount of time. If the light therapy device 12 is in the lead mode 70, the treatment time may be sent to other light therapy devices 12 in the system 10 that are configured to be in the follow mode 80. If the light therapy device 12 is in the neutral mode 90, the treatment time may not be sent to any other light therapy devices 12 in the system 10 and the light therapy device 12 may ignore other incoming instructions.

The plurality of input buttons 110 may also have a play/pause button 114 which, when pressed a first time 800, may be configured to cause at least a portion of the plurality of lights 16 to emit red light and/or near infrared light 802. In some embodiments, the play/pause button 114, when pressed a second time 804, may be configured to cause at least a portion of the plurality of lights 16 to not emit red light and/or near infrared light 806. The play/pause button 114 may start, pause, or continue the treatment time as set by the time button 112. This allows the user to pause the treatment session without having to restart from the beginning. Pressing the play/pause button 114 on light therapy devices 12 configured to be in the lead mode 70 may start the treatment for other light therapy devices 12 in the system 10 including those in follow mode 80. Generally, light therapy devices 12 in the lead mode 70 may send instructions to other light therapy devices 12 in the follow mode 80 to operate in the same way.

Furthermore, the plurality of input buttons 110 may also have a mode button 116. When the mode button 116 is pressed this may change the type of light emitted from at least a portion of the plurality of lights 16 during treatment. For instance, in some embodiments, at least a portion of the plurality of lights 16 may be configured to automatically emit both red light and near infrared light when the treatment starts, but when the mode button 116 is pressed a first time 900 at least a portion of the plurality of lights 16 may be configured to emit red light and not emit near infrared light 902 when treatment starts. In some embodiments, when the mode button 116 is pressed a second time 904 at least a portion of the plurality of lights 16 may be configured to emit near infrared light and not emit red light 906 when treatment starts. Similarly, in other embodiments, a third press of the mode button 116 may configure at least a portion of the plurality of lights 16 to emit both red light and near infrared light. Although only one set of press button commands is specifically mentioned herein, it should be appreciated that any order or combination of button presses may be used. For example, in some embodiments, when the mode button 116 is pressed a first time 900 at least a portion of the plurality of lights 16 may be configured to emit both red light and near infrared light 902 when treatment starts. However, it should be appreciated that any light wavelength or combination of light wavelengths from 100 to 1,000 nanometers (nm), such as UV, blue, green, red, and near-infrared, may be implemented in the system 10 and thereby emitted or not emitted from the plurality of lights 16. Accordingly, any of the input buttons 110 may be arranged and configured to control the plurality of lights 16 to emit and/or not emit light included in any combination of light wavelengths from 100 to 1,000 nm.

With continued reference to FIG. 6b, when the light therapy system 10 has not yet started treatment or is paused it may be difficult to determine if the treatment will consist of red light, near infrared light, or both. To make it easier to determine which lights are active, some embodiments feature a pair of indication lights 120 located on the control panel 100. One light of the pair of indication lights 120 may be labeled red and the other may be labeled near infrared or simply infrared. The pair of indication lights 120 may indicate to a user the type of light that will be emitted when the treatment starts or continues by illuminating one or both indication lights 120. For example, in some embodiments, when the plurality of lights 16 is configured to emit only red light during treatment the indication light labeled red may be illuminated and the indication light labeled infrared may not be illuminated. Similarly, when the plurality of lights 16 is configured to emit only near infrared light during treatment the indication light labeled infrared may be illuminated and the indication light labeled red may not be illuminated. Moreover, when the plurality of lights 16 is configured to emit both red light and near infrared light during treatment the indication light labeled red may be illuminated and the indication light labeled infrared may also be illuminated.

Interpretation

None of the steps described herein is essential or indispensable. Any of the steps can be adjusted or modified. Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1 and embodiments described in other sections may apply to and be combined with embodiments described within the "Topic 1" section.

Some of the devices, systems, embodiments, and processes use computers. Each of the routines, processes, methods, and algorithms described in the preceding sections may be embodied in, and fully or partially automated by, code modules executed by one or more computers, computer processors, or machines configured to execute computer instructions. The code modules may be stored on any type of non-transitory computer-readable storage medium or tangible computer storage device, such as hard drives, solid state memory, flash memory, optical disc, and/or the like. The processes and algorithms may be implemented partially or wholly in application-specific circuitry. The results of the disclosed processes and process steps may be stored, persistently or otherwise, in any type of non-transitory computer storage such as, e.g., volatile or non-volatile storage.

The various features and processes described above may be used independently of one another, or may be combined in various ways. All possible combinations and subcombinations are intended to fall within the scope of this disclosure. In addition, certain method, event, state, or process blocks may be omitted in some implementations. The methods, steps, and processes described herein are also not limited to any particular sequence, and the blocks, steps, or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments can include A, B, and C. The term "and/or" is used to avoid unnecessary redundancy.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein.

What is claimed is:

1. A method for providing a light therapy treatment, comprising:
   providing a first light therapy device comprising a first housing and a first plurality of lights configured to emit at least one of red light and near infrared light;
   providing a second light therapy device comprising a second housing and a second plurality of lights configured to emit at least one of red light and near infrared light;
   communicatively coupling the first light therapy device directly to the second light therapy device;
   emitting at least one of red light and near infrared light from at least a portion of the first plurality of lights and at least a portion of the second plurality of lights;
   placing the first light therapy device in a lead mode; and
   placing the second light therapy device in a follow mode whereby the second light therapy device performs operations as instructed by the first light therapy device.

2. The method of claim 1, wherein the emitting at least one of red light and near infrared light from at least the portion of the first plurality of lights and at least the portion of the second plurality of lights is accomplished using a control panel coupled to the first housing of the first light therapy device.

3. The method of claim 2, further comprising pressing a first input button on the control panel of the first light therapy device, wherein the emitting occurs in response to the pressing.

4. The method of claim 3, further comprising setting a treatment time by pressing a second input button on the control panel of the first light therapy device, wherein the treatment time comprises a duration of time that the first light therapy device and the second light therapy device emit at least one of red light and near infrared light.

5. The method of claim 4, further comprising displaying an indication of the treatment time on a first display located on the control panel of the first light therapy device.

6. The method of claim 5, wherein the treatment time is 20 minutes.

7. The method of claim 4, further comprising increasing the treatment time by pressing the second input button a second time.

8. The method of claim 7, wherein increasing the treatment time comprises increasing the treatment time by the duration of time equal to the treatment time.

9. The method of claim 2, further comprising pausing the emitting in response to pressing a first input button on the control panel of the first light therapy device.

10. The method of claim 1, further comprising:
    selecting the lead mode via a first switch coupled to the first light therapy device, wherein the first light therapy device is placed in the lead mode via the first switch; and
    selecting the follow mode via a second switch coupled to the second light therapy device, wherein the second light therapy device is placed in the follow mode via the second switch.

11. The method of claim 1, further comprising indicating, via a first pair of indication lights on the first light therapy device, whether at least one of red light and near infrared light is being emitted from at least the portion of the first plurality of lights.

12. The method of claim 11, further comprising indicating, via a second pair of indication lights on the second light therapy device, whether at least one of red light and near infrared light is being emitted from at least the portion of the second plurality of lights.

13. The method of claim 1, wherein emitting at least one of red light and near infrared light from at least the portion of the first plurality of lights and at least the portion of the second plurality of lights comprises:
    emitting red light from at least the portion of the first plurality of lights; and
    emitting red light from at least the portion of the second plurality of lights.

14. The method of claim 1, wherein emitting at least one of red light and near infrared light from at least the portion of the first plurality of lights and at least the portion of the second plurality of lights comprises:
    emitting near infrared light from at least the portion of the first plurality of lights; and emitting near infrared light from at least the portion of the second plurality of lights.

15. The method of claim 1, wherein emitting at least one of red light and near infrared light from at least a portion of the first plurality of lights and at least a portion of the second plurality of lights comprises:
    emitting red light from at least the portion of the first plurality of lights; and
    emitting near infrared light from the portion of the second plurality of lights.

16. The method of claim 1, wherein communicatively coupling the first light therapy device directly to the second light therapy device comprises coupling the first light therapy device and the second light therapy device via a wired connection.

17. The method of claim 16, wherein coupling the first light therapy device and the second light therapy device via the wired connection comprises:
    inserting a first end of a communication cable into a first communication port on the first light therapy device; and
    inserting a second end of the communication cable into a second communication port on the second light therapy device.

18. The method of claim 1, wherein communicatively coupling the first light therapy device directly to the second light therapy device comprises coupling the first light therapy device and the second light therapy device via a wireless connection.

19. The method of claim 1, further comprising:
    providing a third light therapy device comprising a third housing and a third plurality of lights configured to emit at least one of red light and near infrared light;
    providing a fourth light therapy device comprising a fourth housing and a fourth plurality of lights configured to emit at least one of red light and near infrared light;
    communicatively coupling each of the third light therapy device and the fourth light therapy device directly to at least one of the first light therapy device and the second light therapy device; and
    emitting at least one of red light and near infrared light from at least a portion of the third plurality of lights and at least a portion of the fourth plurality of lights.

20. The method of claim 19, further comprising:
    providing a fifth light therapy device comprising a fifth housing and a fifth plurality of lights configured to emit at least one of red light and near infrared light;
    providing a sixth light therapy device comprising a sixth housing and a sixth plurality of lights configured to emit at least one of red light and near infrared light;
    communicatively coupling each of the fifth light therapy device and the sixth light therapy device directly to at least one of the first light therapy device, the second light therapy device, the third light therapy device, and the fourth light therapy device; and
    emitting at least one of red light and near infrared light from at least a portion of the fifth plurality of lights and at least a portion of the sixth plurality of lights.

\* \* \* \* \*